(12) United States Patent
Kitagawa

(10) Patent No.: US 11,241,016 B2
(45) Date of Patent: Feb. 8, 2022

(54) DIVALENT IRON SUPPLY AGENT

(71) Applicant: ASAHI GROUP HOLDINGS, LTD., Tokyo (JP)

(72) Inventor: Takanori Kitagawa, Tokyo (JP)

(73) Assignee: ASAHI GROUP HOLDING, LTD., Tokyo (JP)

( * ) Notice: Subject to any disclaimer, the term of this patent is extended or adjusted under 35 U.S.C. 154(b) by 6 days.

(21) Appl. No.: 16/613,869

(22) PCT Filed: Mar. 5, 2018

(86) PCT No.: PCT/JP2018/008374
§ 371 (c)(1),
(2) Date: Nov. 15, 2019

(87) PCT Pub. No.: WO2018/216303
PCT Pub. Date: Nov. 29, 2018

(65) Prior Publication Data
US 2020/0196610 A1  Jun. 25, 2020

(30) Foreign Application Priority Data

May 22, 2017 (JP) .............................. JP2017-101173

(51) Int. Cl.
| | |
|---|---|
| *A01N 63/32* | (2020.01) |
| *A01N 59/16* | (2006.01) |
| *A01N 59/26* | (2006.01) |
| *A01N 59/02* | (2006.01) |
| *A01N 59/08* | (2006.01) |
| *A01N 59/00* | (2006.01) |
| *A01N 65/08* | (2009.01) |
| *A61L 2/238* | (2006.01) |
| *C05B 17/00* | (2006.01) |
| *C05D 9/02* | (2006.01) |
| *A01P 3/00* | (2006.01) |

(52) U.S. Cl.
CPC ............ *A01N 63/32* (2020.01); *A01N 59/16* (2013.01); *A01N 59/26* (2013.01); *A61L 2/238* (2013.01); *C05B 17/00* (2013.01); *C05D 9/02* (2013.01); *A01P 3/00* (2021.08)

(58) Field of Classification Search
None
See application file for complete search history.

(56) References Cited

U.S. PATENT DOCUMENTS

| | | | |
|---|---|---|---|
| 5,766,929 A | 6/1998 | Orolin et al. | |
| 6,379,413 B1 * | 4/2002 | Miele | C05D 9/02 71/17 |
| 8,951,326 B2 * | 2/2015 | Kitagawa | C05B 17/00 71/11 |
| 2013/0017270 A1 | 1/2013 | Morikawa | |
| 2014/0031196 A1 | 1/2014 | Morikawa et al. | |
| 2014/0250961 A1 | 9/2014 | Kitagawa et al. | |

FOREIGN PATENT DOCUMENTS

| | | |
|---|---|---|
| CN | 105061000 | 11/2015 |
| EP | 2 725 001 | 4/2014 |
| JP | 2-142760 | 5/1990 |
| JP | 2002-138031 | 5/2002 |
| JP | 2002-325567 | 11/2002 |
| JP | 2004-244324 | 9/2004 |
| JP | 2004-256333 | * 9/2004 |
| JP | 2013-241299 | 12/2013 |
| JP | 5733781 | 4/2015 |
| JP | 2017-012113 | 1/2017 |
| WO | 2011/121832 | 10/2011 |
| WO | 2013/002250 | 1/2013 |
| WO | 2013/094235 | 6/2013 |

OTHER PUBLICATIONS

Derwent Abstract 2004-657776 (2004); abstracting JP 2004-256333 (2004).*
Potassium Silicate Biopesticides Registration Action Document, U.S. Environmental Protection Agency, Office of Pesticide Programs, pp. 1-30, Sep. 7, 2007.*
Wu, L. et al., "Slow-release potassium silicate fertilizer with the function of superabsorbent and water retention," Industrial & Engineering Chemistry, vol. 46, pp. 6494-6500 (2007).*
Extended European Search Report dated Jan. 28, 2021 in corresponding European Patent Application No. 18806716.9.
International Search Report (ISR) dated Apr. 24, 2018 in International (PCT) Application No. PCT/JP2018/008374.
Translation of The International Preliminary Report on Patentability dated Dec. 5, 2019 in International (PCT) Application No. PCT/JP2018/008,374.

* cited by examiner

*Primary Examiner* — John Pak
(74) *Attorney, Agent, or Firm* — Wenderoth, Lind & Ponack, L.L.P.

(57) ABSTRACT

[Problem] To provide a new technology with which it is possible to further increase a supply amount of divalent iron. [Solution] Provided is a divalent iron supply agent that contains: a hydrothermal reaction treatment product of a mixture containing at least one of yeast, a yeast extract, and a yeast cell wall, at least one of phosphoric acid and a phosphoric acid compound, and at least one of potassium and a potassium compound; and an iron supply raw material.

5 Claims, No Drawings

DIVALENT IRON SUPPLY AGENT

TECHNICAL FIELD

The present invention relates to a divalent iron supplying agent which can supply divalent iron contributing to sterilization when applied to, for example, soil.

BACKGROUND ART

Paddy rice cultivation is an excellent cultivation technique free from soilborne diseases and replant failures. In this cultivation technique, since the flooded paddy field soil is in a reduced state, trivalent iron in the soil is reduced to divalent iron. It is known that owing to the sterilization action of this divalent iron, pathogenic bacteria such as Fusarium fungus die, so that the above cultivation technique is a cultivation technique free from soilborne diseases and replant failures.

On the other hand, since soil of upland fields other than paddy fields, and turf fields such as golf course, baseball field and soccer field is not in a reduced state, all of iron exists as trivalent iron. On that account, soil pathogenic bacteria cannot be restrained, and soilborne diseases are spreading. Moreover, the soil is further oxidized by excessive application of chemical fertilizers, and in such soil, divalent iron cannot exist more.

In order to improve the above situation, a divalent iron material, a chelating material, etc. are on the market, but they have insufficient stability. These divalent iron material and chelating material, etc. are oxidized and converted into trivalent iron as soon as they come into contact with oxygen, and therefore, they cannot be supplied to soil as divalent iron. On that account, materials to make it possible to supply a larger amount of divalent iron have been proposed (for example, Patent Literature 1). In Patent Literature 1, the amount of divalent iron supplied from an iron feedstock is increased by using ground roasted coffee beans and/or tea leaves as feedstocks functioning as reduction action components, and mixing a dry product of these feedstocks functioning as reduction action components with an iron feedstock containing divalent or trivalent iron in the presence of water to react them with each other.

CITATION LIST

Patent Literature

Patent Literature 1: Japanese Patent No. 5733781

SUMMARY OF INVENTION

Technical Problem

However, a method for supplying divalent iron in a larger amount has been desired.

It is an object of the present invention to provide a novel technique capable of increasing the amount of divalent iron supplied.

Solution to Problem

The present inventors have earnestly studied in the light of the above problem. As a result, the present inventors have found that by constituting a mixture which comprises a hydrothermal reaction treatment product of a mixture comprising at least one of a yeast, a yeast extract and a yeast cell wall, at least one of phosphoric acid and a phosphate compound, and at least one of potassium and a potassium compound, and an iron feedstock such as a divalent iron salt or a trivalent iron salt, divalent iron can be more stably supplied to soil or the like, whereby the amount of the divalent iron supplied can be increased, and thus, the present inventor has completed the present invention.

The gist of the present invention is as follows.

[1] A divalent iron supplying agent comprising: a hydrothermal reaction treatment product of a mixture comprising at least one of a yeast, a yeast extract and a yeast cell wall, at least one of phosphoric acid and a phosphate compound, and at least one of potassium and a potassium compound; and an iron feedstock.

[2] The divalent iron supplying agent according to [1], further comprising one or more substances selected from the group consisting of a silicate source, used coffee grounds and used tea leaves.

[3] The divalent iron supplying agent according to [1] or [2], further comprising a silicate source.

[4] The divalent iron supplying agent according to any one of [1] to [3], further comprising at least one of used coffer grounds and used tea leaves.

[5] A method for increasing an amount of divalent iron derived from an iron feedstock, comprising reacting a hydrothermal reaction treatment product of a mixture comprising at least one of a yeast, a yeast extract and a yeast cell wall, at least one of phosphoric acid and a phosphate compound, and at least one of potassium and a potassium compound with the iron feedstock in the presence of water.

Advantageous Effect of Invention

According to the present invention, a novel technique capable of further increasing the amount of divalent iron supplied can be provided.

DESCRIPTION OF EMBODIMENT

One embodiment of the present invention is described in detail hereinafter.

The present embodiment relates to a divalent iron supplying agent, comprising a hydrothermal reaction treatment product of a mixture comprising at least one of a yeast, a yeast extract and a yeast cell wall, at least one of phosphoric acid and a phosphate compound, and at least one of potassium and a potassium compound, and an iron feedstock.

In the present embodiment, the hydrothermal reaction treatment product and the iron feedstock react with each other to reduce trivalent iron, whereby the amount of divalent iron (divalent iron ions) derived from the iron feedstock increases, and the amount of divalent iron supplied increases more than before.

The divalent iron derived from the iron feedstock includes not only divalent iron released from the iron feedstock but also divalent iron converted from trivalent iron which has been released from the iron feedstock and divalent iron further converted from trivalent iron which has been converted from divalent iron released from the iron feedstock.

In the present specification, the iron feedstock is not particularly limited as long as it is a substance capable of releasing divalent iron or trivalent iron which is reduced to divalent iron, in the presence of water, and the iron feedstock can be appropriately set by a person skilled in the art. Specific examples thereof include salts of divalent iron, such as iron(II) sulfate, salts of trivalent iron such as iron(III) chloride and iron(III) sulfate, steel slag, and soil containing iron, and the divalent iron supplying agent of the present embodiment may contain, for example, one or more of them as the iron feedstocks.

The hydrothermal reaction treatment product is disclosed in, for example, WO 2013/094235, and can be produced from conventionally known materials in accordance with the method disclosed in WO 2013/094235. The international application related to WO 2013/094235 has been registered as, for example, Japanese Patent No. 5555818 in Japan.

The yeast, the yeast extract or the yeast cell wall for use as a raw material of the hydrothermal reaction treatment product is not particularly limited, and can be derived from at least one selected from the group consisting of muddy beer yeast, pressed beer yeast, dry beer yeast, a beer yeast suspension, a dry yeast cell wall, a yeast cell wall suspension and a beer yeast-containing inorganic substance.

The phosphoric acid or the phosphate compound may be used singly or as a mixture of two or more. As the phosphoric acid or the phosphate compound, for example, a phosphate compound conventionally known as a component of a fertilizer can be used. Specifically, any of various soluble or citric acid-soluble fertilizers only needs to be used as the fertilizer, and examples of the phosphate compounds include superphosphate of lime and double or triple superphosphate of lime each of which is obtained by treating rock phosphate with sulfuric acid to obtain soluble phosphoric acid, phosphorous acid, and a fused phosphate fertilizer and a calcined phosphate fertilizer each of which is a mixture.

Potassium or the potassium compound may be used singly or as a mixture of two or more. As potassium or the potassium compound, for example, a potassium compound conventionally known as a component of a fertilizer can be used. Specific examples thereof include potassium chloride, potassium sulfate, potassium hydroxide, potassium phosphite and potassium nitrate.

The hydrothermal reaction treatment product can be obtained by subjecting a mixture containing the following three components (a), (b) and (c) to hydrothermal reaction treatment (superheated steam treatment).

(a) One or more selected from the group consisting of a yeast, a yeast extract and a yeast cell wall
(b) Phosphoric acid and/or a phosphate compound
(c) Potassium and/or a potassium compound In the present specification, the hydrothermal reaction treatment means a method in which superheated steam is generated by heating and applying pressure, and by the influence of the superheated steam generated, properties of the object are changed.

The temperature to generate superheated steam is preferably 120° C. or higher and 220° C. or lower, and more preferably 150° C. or higher and 210° C. or lower. The pressure to generate superheated steam is preferably 0.9 MPa or more and 1.9 MPa or less, and more preferably 1.2 MPa or more and 1.8 MPa or less. In particular, hydrothermal reaction treatment carried out at a pressure of 0.9 MPa or more and 1.9 MPa or less and a temperature of 120° C. or higher and 220° C. or lower is preferable, hydrothermal reaction treatment carried out at a pressure of 0.9 MPa or more and 1.9 MPa or less and a temperature of 150° C. or higher and 210° C. or lower is more preferable, and hydrothermal reaction treatment carried out at a pressure of 1.2 MPa or more and 1.8 MPa or less and a temperature of 150° C. or higher and 210° C. or lower is still more preferable.

The mixing ratio of the three components (a), (b) and (c) is not particularly limited, and can be appropriately set by a person skilled in the art. For example, based on 100 parts by weight of the component (a), the amount of the component (b) can be specified to more than 0 and 135 parts or less by weight, and the amount of the component (c) can be specified to more than 0 and 100 parts or less by weight.

The divalent iron supplying agent of the present embodiment can be a mixture containing the above-mentioned iron feedstock and hydrothermal reaction treatment product. The mixing method, the mixing ratio, etc. are not particularly limited and can be appropriately set by a person skilled in the art, and for example, based on 100 parts by weight of the iron feedstock, the amount of the hydrothermal reaction treatment product can be specified to 1 to 20000 parts by weight.

The divalent iron supplying agent of the present embodiment may further contain, in addition to the iron feedstock and the hydrothermal reaction treatment product, other components within a range where the object of the present invention can be achieved.

For example, the divalent iron supplying agent of the present embodiment can be in the form of a solution or a suspension containing the iron feedstock and the hydrothermal reaction treatment product, and hence, the divalent iron supplying agent may contain water.

In addition, the divalent iron supplying agent of the present embodiment may contain minor elements, corrosion products, organic acids, amino acid, diatomaceous earth, zeolite, foamed cellular concrete, fertilizer raw materials, agricultural chemicals, or the like.

The divalent iron supplying agent of the present embodiment preferably further contains one or more substances selected from the group consisting of a silicate source, used coffee grounds and used tea leaves. The divalent iron supplying agent of the present embodiment more preferably further contains the silicate source among them. By allowing the divalent iron supplying agent of the present embodiment to further contain one or more substances selected from the group consisting of a silicate source, used coffee grounds and used tea leaves, a larger amount of divalent iron can be supplied.

The silicate source is not particularly limited as long as it is a substance capable of supplying silicate (silicate ions) in the presence of water, and examples thereof include minerals containing silicic acid, such as Bakuhanseki, foamed cellular concrete, rice husks and potassium silicate.

As the used coffee grounds (residue left after extraction of coffee extract from roasted coffee beans) and the used tea leaves (residue left after extraction of tea component of green tea, black tea, oolong tea or the like), publicly known ones can be utilized, and they are not particularly limited.

There is no specific limitation on the form of the divalent iron supplying agent of the present embodiment, and for example, it may be a liquid such as a solution, as previously described, or may be a solid produced through a step of drying or the like. When the divalent iron supplying agent in a solid state is applied to soil or the like, reaction of the hydrothermal reaction treatment product with the iron feedstock proceeds in the presence of water contained in the soil or the like to which the divalent iron supplying agent has been applied.

There is no specific limitation on the application target of the divalent iron supplying agent of the present embodiment, and the application target is, for example, soil of upland fields and turf fields. When the divalent iron supplying agent of the present embodiment is applied to soil, the amount of the divalent iron supplying agent of the present embodiment applied is not particularly limited and can be appropriately set by a person skilled in the art. For example, the divalent iron supplying agent of the present embodiment in an amount of 1 kg or more and 1000 kg or less may be mixed with soil having an area of 10 ares.

As described above, according to the present embodiment, the amount of divalent iron derived from the iron feedstock increases owing to the action of the hydrothermal reaction treatment product, and therefore, a larger amount of divalent iron can be supplied. As a result, when the divalent iron supplying agent of the present embodiment is applied to, for example, soil, a greater sterilization action is expected.

EXAMPLES

The present invention is more specifically described with reference to the following examples, but the present invention is in no way limited to those examples.

Reference Example 1: Hydrothermal Reaction Treatment Product of Mixture of Yeast Cell Wall, Phosphoric Acid and Potassium Compound In a magnetic stirring type hydrothermal reaction vessel, 143.6 g of distilled water was introduced, and thereafter, 25.4 g of a yeast cell wall (Asahi Food & Healthcare, Ltd.), 16.2 g of 85% phosphoric acid and 14.8 g of potassium sulfate were introduced. The lid was closed, then stirring and mixing were carried out, and thereafter, temperature raising was started. Under the conditions of a pressure of not less than 1.6 MPa and a temperature of 180° C., treatment was carried out for 10 minutes to obtain a hydrothermal reaction treatment product 1.

Example 1

To 20 ml of a 0.1% iron(III) chloride hexahydrate (Wako Pure Chemical Industries, Ltd.) aqueous solution, 0.4 ml of the hydrothermal reaction treatment product 1 was added, and thereafter, they were stirred and mixed to prepare a reaction solution. After this reaction solution was allowed to stand for 2 minutes at room temperature, the solution was filtered through a filter of 0.45 µm, and divalent iron in the resulting filtrate was determined using a test paper for divalent iron analysis (KYORITSU CHEMICAL-CHECK Lab., Corp.).

Comparative Example 1

To 20 ml of a 0.1% iron(III) chloride hexahydrate (Wako Pure Chemical Industries, Ltd.) aqueous solution, 0.4 ml of a silicic acid material (A-One Silica, manufactured by Seiwa Fertilizer Ind. Co., Ltd.) was added, and thereafter, they were stirred and mixed to prepare a reaction solution. After this reaction solution was allowed to stand for 2 minutes at room temperature, the solution was filtered through a filter of 0.45 µm, and divalent iron in the resulting filtrate was determined using a test paper for divalent iron analysis (KYORITSU CHEMICAL-CHECK Lab., Corp.).

Example 2

To 20 ml of a 0.1% iron(III) chloride hexahydrate (Wako Pure Chemical Industries, Ltd.) aqueous solution, 0.4 ml of the hydrothermal reaction treatment product 1 and 0.4 ml of a silicic acid material (A-One Silica, manufactured by Seiwa Fertilizer Ind. Co., Ltd.) were added, and thereafter, they were stirred and mixed to prepare a reaction solution. After this reaction solution was allowed to stand for 2 minutes at room temperature, the solution was filtered through a filter of 0.45 µm, and divalent iron in the resulting filtrate was determined using a test paper for divalent iron analysis (KYORITSU CHEMICAL-CHECK Lab., Corp.).

Comparative Example 2

To 20 ml of a 0.1% iron(III) chloride hexahydrate (Wako Pure Chemical Industries, Ltd.) aqueous solution, 4 g of used coffee grounds having a water content of 60% (Asahi Soft Drinks Co., Ltd.) were added, and thereafter, they were stirred and mixed to prepare a reaction solution. After this reaction solution was allowed to stand for 2 minutes at room temperature, the solution was filtered through a filter of 0.45 µm, and divalent iron in the resulting filtrate was determined using a test paper for divalent iron analysis (KYORITSU CHEMICAL-CHECK Lab., Corp.).

Example 3

To 20 ml of a 0.1% iron(III) chloride hexahydrate (Wako Pure Chemical Industries, Ltd.) aqueous solution, 0.4 ml of the hydrothermal reaction treatment product 1 and 4 g of used coffee grounds having a water content of 60% (Asahi Soft Drinks Co., Ltd.) were added, and thereafter, they were stirred and mixed to prepare a reaction solution. After this reaction solution was allowed to stand for 2 minutes at room temperature, the solution was filtered through a filter of 0.45 µm, and divalent iron in the resulting filtrate was determined using a test paper for divalent iron analysis (KYORITSU CHEMICAL-CHECK Lab., Corp.).

Comparative Example 3

To 20 ml of a 0.1% iron(III) chloride hexahydrate (Wako Pure Chemical Industries, Ltd.) aqueous solution, 4 g of used tea leaves having a water content of 60% (Asahi Soft Drinks Co., Ltd.) were added, and thereafter, they were stirred and mixed to prepare a reaction solution. After this reaction solution was allowed to stand for 2 minutes at room temperature, the solution was filtered through a filter of 0.45 µm, and divalent iron in the resulting filtrate was determined using a test paper for divalent iron analysis (KYORITSU CHEMICAL-CHECK Lab., Corp.).

Example 4

To 20 ml of a 0.1% iron(III) chloride hexahydrate (Wako Pure Chemical Industries, Ltd.) aqueous solution, 0.4 ml of the hydrothermal reaction treatment product 1 and 4 g of used tea leaves having a water content of 60% (Asahi Soft Drinks Co., Ltd.) were added, and thereafter, they were stirred and mixed to prepare a reaction solution. After this reaction solution was allowed to stand for 2 minutes at room temperature, the solution was filtered through a filter of 0.45 µm, and divalent iron in the resulting filtrate was determined using a test paper for divalent iron analysis (KYORITSU CHEMICAL-CHECK Lab., Corp.).

The determination results of the examples and the comparative examples are set forth in Table 1. As a result, it has been shown that by mixing the hydrothermal reaction treatment product 1 with iron(III) chloride hexahydrate, trivalent iron was converted into divalent iron, and the amount of the divalent iron increased. Moreover, it can be understood that by mixing a mixed solution of the hydrothermal reaction treatment product 1 and iron(III) chloride hexahydrate with a silicic acid material, used coffee grounds or used tea leaves, trivalent iron was further converted into divalent iron.

TABLE 1

| Sample name | Divalent iron concentration (mg/L) |
| --- | --- |
| 0.1% Iron (III) chloride hexahydrate aqueous solution | 0 |
| Example 1 | 10 |
| Comparative example 1 | 0 |
| Example 2 | 30 |
| Comparative example 2 | 5 |
| Example 3 | 20 |
| Comparative example 3 | 5 |
| Example 4 | 15 |

INDUSTRIAL APPLICABILITY

The divalent iron supplying agent of the present invention can convert trivalent iron into divalent iron, and therefore, it can supply divalent iron more stably as compared with conventional divalent iron supplying agents. The divalent iron supplying agent of the present invention is expected to contribute to restoration of soil of, for example, upland fields where soilborne diseases are spreading, and turf fields such as golf course, baseball field and soccer field.

The invention claimed is:

1. A divalent iron supplying agent comprising:
   a hydrothermal reaction treatment product of a mixture comprising at least one selected from the group consisting of a yeast, a yeast extract and a yeast cell wall, at least one selected from the group consisting of phosphoric acid and a phosphate compound, and at least one selected from the group consisting of potassium and a potassium compound;
   an iron feedstock; and
   one or more substances selected from the group consisting of a silicate source, used coffee grounds and used tea leaves,
   wherein the hydrothermal reaction treatment product is obtained by subjecting the mixture to a hydrothermal reaction treatment at a pressure of 0.9 MPa or more and 1.9 MPa or less and a temperature of 120° C. or higher and 220° C. or lower.

2. The divalent iron supplying agent according to claim 1, comprising the silicate source.

3. The divalent iron supplying agent according to claim 1, further comprising at least one selected from the group consisting of the used coffercoffee grounds and the used tea leaves.

4. The divalent iron supplying agent according to claim 2, further comprising at least one selected from the group consisting of the used coffee grounds and the used tea leaves.

5. A method for increasing an amount of divalent iron derived from an iron feedstock, comprising reacting a hydrothermal reaction treatment product of a mixture comprising at least one selected from the group consisting of a yeast, a yeast extract and a yeast cell wall, at least one selected from the group consisting of phosphoric acid and a phosphate compound, and at least one selected from the group consisting of potassium and a potassium compound with the iron feedstock in the presence of water and one or more substances selected from the group consisting of a silicate source, used coffee grounds and used tea leaves,
   wherein the hydrothermal reaction treatment product is obtained by subjecting the mixture to a hydrothermal reaction treatment at a pressure of 0.9 MPa or more and 1.9 MPa or less and a temperature of 120° C. or higher and 220° C. or lower.

* * * * *